United States Patent
Schanen et al.

(10) Patent No.: US 7,217,842 B2
(45) Date of Patent: May 15, 2007

(54) CATALYSTS FOR NUCLEOPHILIC SUBSTITUTION, SYNTHESIS THEREOF, COMPOSITION CONTAINING THEM AND USE THEREOF

(75) Inventors: Vincent Schanen, Lyons (FR); Henri-Jean Cristau, Saint-Aunes (FR); Marc Taillefer, Vailhauques (FR)

(73) Assignee: Rhodia-Chimie, Aubervilliers (FR)

( * ) Notice: Subject to any disclaimer, the term of this patent is extended or adjusted under 35 U.S.C. 154(b) by 278 days.

(21) Appl. No.: 10/472,912

(22) PCT Filed: Apr. 12, 2002

(86) PCT No.: PCT/FR02/01286

§ 371 (c)(1),
(2), (4) Date: Mar. 1, 2004

(87) PCT Pub. No.: WO02/092226

PCT Pub. Date: Nov. 21, 2002

(65) Prior Publication Data

US 2004/0147390 A1 Jul. 29, 2004

(30) Foreign Application Priority Data

Apr. 12, 2001 (FR) .................................. 01 05034
Apr. 11, 2002 (FR) .................................. 02 04522

(51) Int. Cl.
*C07F 9/02* (2006.01)
*B01J 31/00* (2006.01)

(52) U.S. Cl. .................... 568/10; 564/12; 502/162; 502/167

(58) Field of Classification Search ............ 502/162, 502/167; 568/17; 564/12
See application file for complete search history.

(56) References Cited

U.S. PATENT DOCUMENTS

| 4,069,262 | A | * | 1/1978 | Kunz | ............ 568/937 |
| 4,140,719 | A | * | 2/1979 | Tull et al. | ............ 564/417 |
| 5,045,632 | A | | 9/1991 | Parker | ............ 562/45 |
| 5,401,814 | A | | 3/1995 | Schomaker et al. | ............ 525/523 |

FOREIGN PATENT DOCUMENTS

DE 197 02 282 7/1998
EP 0523 671 1/1993

OTHER PUBLICATIONS

International Search Report.

* cited by examiner

*Primary Examiner*—David Sample

(57) ABSTRACT

The invention concerns novel catalysts for aromatic nucleophilic substitution. Said catalysts are compounds of the general formula (I), wherein: $R_1$, $R_2$, $R_3$, $R_4$, $R_5$, and $R_6$, identical or different, are selected among hydrocarbon radicals; the Pn's, advantageously the same, are selected among metalloid elements of column V of a period higher than nitrogen; Z is a metalloid element of column V, advantageously distinct from Pn; preferably a nitrogen (N, P, As, Sb). The invention is applicable to organic synthesis 10 Claims, 1 Drawing Sheet

CATALYSTS FOR NUCLEOPHILIC SUBSTITUTION, SYNTHESIS THEREOF, COMPOSITION CONTAINING THEM AND USE THEREOF

This application is an application under 35 U.S.C. Section 371 of International Application Number PCT/02/01286 filed on Apr. 12, 2002.

The present invention relates to a novel method for performing nucleophilic substitutions, especially of $SN_{Ar}$ type, and is more particularly directed toward novel catalysts. Although the effect is less pronounced, it is also directed toward the use of these catalysts for $SN_2$ reactions.

The invention is more particularly of interest to aromatic nucleophilic substitution reactions involving the following reaction scheme:
attack of a nucleophilic agent on an aromatic substrate with creation of a bond between said nucleophilic agent and said substrate, on a carbon bearing a leaving group, so as to form an intermediate compound known as a Meisenheimer intermediate (when the nucleophile is an anion) or equivalent, and then
loss of said leaving group.

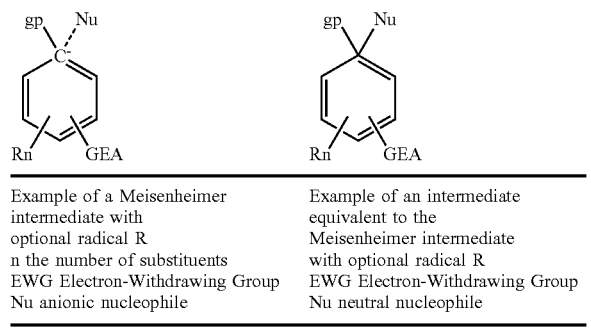

Example of a Meisenheimer intermediate with
optional radical R
n the number of substituents
EWG Electron-Withdrawing Group
Nu anionic nucleophile Example of an intermediate equivalent to the
Meisenheimer intermediate
with optional radical R
EWG Electron-Withdrawing Group
Nu neutral nucleophile Examples of $SN_{Ar}$ intermediates will be given below:

Reactions of this type are particularly advantageous for obtaining halogenated aromatic derivatives and are especially used to perform exchanges between fluorine, on the one hand, and halogen(s) of a higher row or pseudohalogen on an aromatic substrate.

The leaving group may thus be a nitro group, advantageously a pseudohalogen, or, preferably, a halogen atom, especially having an atomic number higher than that of fluorine.

The term "pseudohalogen" is intended to denote a group which, on leaving, leads to an oxygenated anion, the anionic charge being borne by the chalcogen atom and the acidity of which is at least equal to that of acetic acid, advantageously to the second acidity of sulfuric acid, and preferably to that of trifluoroacetic acid. In order to determine the position on the acidity scale, reference should be made to the pKa values for the average to strong acidities from carboxylic acids up to acetic acid and to determine the position on the scale of Hammett constants (see FIG. 1) starting from trifluoroacetic acid.

As illustrations of pseudohalogens of this type, mention may be made in particular of sulfinic and sulfonic acids, which are perhalogenated on the carbon bearing sulfur, and also carboxylic acids perfluorinated α to the carboxylic function.

When the leaving group is a nitro group, this group is generally replaced with a chlorine or fluorine atom. However, most of these reagents make it necessary to work at very high temperatures and the mechanism is not always found to be a nucleophilic substitution. Moreover, loss of the nitro group leads to the formation of oxygenated and halogenated nitrogen derivatives that are particularly aggressive with regard to the substrate, or even explosive.

As regards the variant involving the substitution of a halogen atom present on an aromatic nucleus with another halogen atom, this generally requires at least a partial deactivation of said nucleus. To this end, the aryl radical to be converted is preferably electron-poor and has an electron density at most equal to that of benzene, and at most in the region of that of a chlorobenzene, preferably a dichlorobenzene.

This depletion may be due to the presence in the aromatic ring (six-membered) of a hetero atom, for instance in pyridine or quinoline (the depletion in this case involves a six-membered ring). In this particular case, the depletion is large enough for the substitution reaction to take place very easily and does not require any particular associated activation. The electron-poor state may also be induced with electron-withdrawing substituents present on this aromatic ring. These substituents are preferably chosen from groups that withdraw via an inductive effect or via a mesomeric effect as defined in the reference organic chemistry book "Advanced Organic Chemistry" by J. March, 3rd edition, published by Willey, 1985 (cf. especially pages 17 and 238). As illustrations of these electron-withdrawing groups, mention may be made especially of $NO_2$, quaternary ammonium, Rf and especially $CF_3$, CHO, CN and COY groups with Y possibly being a chlorine, bromine or fluorine atom or an alkyloxy group.

The halogen—halogen exchange reactions mentioned above in fact constitute the main synthetic route for gaining access to fluorinated aromatic derivatives.

Thus, one of the techniques most widely used for manufacturing a fluorinated derivative consists in reacting a halogenated, generally a chlorinated, aromatic derivative, to exchange the halogen(s) with one or more fluorine(s) of mineral origin. An alkali metal fluoride is generally used, usually one of high atomic weight, for instance sodium fluoride and especially potassium, cesium and/or rubidium fluoride.

In general, the fluoride used is potassium fluoride, which constitutes a satisfactory economic compromise.

Under these conditions, many processes, for instance those described in the French certificate of addition No. 2 353 516 and in the article Chem. Ind. (1978)-56 have been proposed and used industrially to obtain aryl fluorides, on which aryls are grafted electron-withdrawing groups, or alternatively aryls that are naturally electron-poor, for instance pyridine nuclei.

However, except in the case where the substrate is particularly adapted to this type of synthesis, this technique has drawbacks, the main of which are those that will be analyzed hereinbelow.

The reaction is slow and, on account of a long residence time, requires large investments. This technique, as has already been mentioned, is generally used at high temperatures that may be up to about 250° C., or even 300° C. in the case of electron-poor nuclei, ie in the zone in which the stablest organic solvents begin to decompose.

The yields remain relatively mediocre unless particularly expensive reagents are used, for instance fluorides of an alkali metal with an atomic mass higher than that of potassium.

Finally, given the price of these alkali metals, their industrial use is justifiable only for products of high added value and when the improvement in the yield and the kinetics justify it, which is rarely the case.

To solve or overcome these difficulties, many improvements have been proposed. Thus, novel catalysts are proposed, and mention may be made especially of tetradialkylaminophosphoniums and especially those described in the patent applications filed in the name of the German company Hoechst and its subsidiary companies Clariant and Aventis (for example U.S. Pat. No. 6,114,589; U.S. Pat. No. 6,103,659; etc.) and in the patent applications filed in the name of the company Albemarle.

These novel catalysts do, admittedly, present a number of advantages over common catalysts, but afford no advantage in terms of their price and their complexity.

Consequently, one of the aims of the present invention is to provide nucleophilic substitution catalysts that especially allow a catalysis of $SN_2$ and above all $SN_{Ar}$ reactions.

Another aim of the present invention is to provide nucleophilic substitution catalysts that especially allow a catalysis of $SN_{Ar}$ reactions, even when the nucleus that is the site of said $SN_{Ar}$ is only weakly electron-poor.

Another aim of the present invention is to provide nucleophilic substitution catalysts that are also phase-transfer agents.

Another aim of the present invention is to provide nucleophilic substitution catalysts that have a relatively high decomposition temperature, for example at least equal to 200° C., advantageously 250° C. and even 300° C.

These aims, and others which will emerge hereinbelow, are achieved by means of use, as a catalyst for nucleophilic substitution, of a compound of general formula (I):

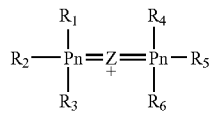

in which:
- $R_1$, $R_2$, $R_3$, $R_4$, $R_5$ and $R_6$, which may be identical or different, are chosen from hydrocarbon-based radicals, one of the radicals $R_1$ to $R_6$ possibly being a hydrogen when the other radicals $R_1$ to $R_6$ are such that the molecule contains more than one and preferably more than two sequence(s) Pn=Z=Pn (in this case, one, or more, Pn may be common to several sequences and Pn is advantageously P and Z is advantageously N);
- the Pn, which are advantageously the same, are chosen from the metalloid elements of column V from a period higher than that of nitrogen;
- Z is a metalloid element from column V, which is advantageously different than Pn, preferably a nitrogen (N, P, As or Sb).

The fact that one of the radicals $R_1$ to $R_6$ is hydrogen is not preferred.

The compounds of formula (I) may be neutral, and in this case they are amphoteric, in other words they bear within the same molecule the cationic function shown in formula (I) and the anionic function that ensures electrical neutrality; however, the compounds of formula (I) that are the easiest to use are cationic compounds and are advantageously introduced in the form of a salt of formula (II):

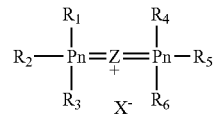

in which:
- $X^-$ is a counterion chosen from anions and mixtures of anions, which anions and mixtures of anions are advantageously chosen from monovalent anions;
- said hydrocarbon-based radicals $R_1$, $R_2$, $R_3$, $R_4$, $R_5$ and $R_6$ are generally chosen from:
    - alkyls;
    - optionally substituted aryls;
    - amino and imino groups, advantageously in which the nitrogen linked to a Pn does not bear hydrogen; among the amino groups, N,N-dialkylamino, N,N-diarylamino and N-aryl-N-alkylamino groups are preferably chosen; among the imino groups that are particularly suitable are mono- and diarylketimino, phosphinimino, and especially trialkyl-, dialkylaryl-, diarylalkyl- and triarylphosphinimino, derivatives of amidine type [of formula >N—C(—)=N— in which (—) represents an open bond] including cyclic forms and including guanidines [(>N—)$_2$C=N—)] may be attached to the Pn via their amine function or via their imine function;
    - phosphino groups, such as dialkylphosphino, alkylarylphosphino and especially diarylphosphino; however, especially when Pn is phosphorus, it is preferable for there to be not more than two and advantageously not more than one such group per Pn atom;
    - hydrocarbyloxy groups;
    - a polymer arm.

As will be seen later, the compounds in which the radicals $R_4$, $R_5$ or even $R_6$ are phosphinimino are easy to synthesize. Among these phosphinimino groups, mention may be made of those in which the phosphorus bears aryl, alkyl or dialkylamino groups.

The aryl groups forming part of the above compound are advantageously homocyclic, taken in the sense antonymous to heterocyclic.

The term "alkyl" is taken in its etymological sense as an alcohol residue from which the OH function has been removed. Thus, it essentially comprises radicals in which the free bond is borne by a carbon atom sp$^3$ hybridization, this carbon atom being linked only to carbons or hydrogens. In the context of the present invention, among the alkyls that may also be mentioned are the compounds of formula $C_nH_{2n+1}$, alkyls which are substituted with atoms and/or functions (depending on the application, it is preferable, in order to avoid side reactions, to select functions that are inert under the working conditions of the invention) and especially those bearing ether function(s) and in particular the mono-, oligo- or polyethoxylated chains derived from epoxides, especially of ethylene and/or of a peralkylated amine function, those which are substituted with halogens, and those bearing one or more aromatic nuclei.

Said alkyls may also bear quaternary ammonium or phosphonium functions.

Except when they represent an arm, the radicals $R_1$, $R_2$, $R_3$, $R_4$, $R_5$ and $R_6$ advantageously contain not more than 20 carbon atoms, and, unless it is linked to a polymer, the molecule comprises in total not more than 100 carbon atoms and preferably not more than 60 carbon atoms.

It is preferable for not more than 2 of the radicals $R_1$, $R_2$, $R_3$, $R_4$, $R_5$ and $R_6$ to represent a polymer arm; this arm is linked to the corresponding Pn atom via a bond with a carbon atom of aliphatic or aromatic nature or via a bond with an imino or amino group.

However, it is more practical to use molecules that are not linked to a polymer.

For reasons of ease of synthesis, it is preferable for $R_1$, $R_2$ and $R_3$ to be identical. This is likewise the case for $R_4$, $R_5$ and $R_6$.

The radicals $R_1$, $R_2$, $R_3$, $R_4$, $R_5$ and $R_6$ may be linked together and may form rings.

In particular:

$R_1$, $R_2$ and $R_3$ may be linked together and may form rings, and $R_4$, $R_5$ and $R_6$ may be linked together and may form rings.

When the Pn are the same, the synthesis of the catalysts in which the radicals $R_1$, $R_2$, $R_3$, $R_4$, $R_5$ and $R_6$ are the same is easier and therefore less expensive. They are therefore preferred in this respect. However, the activity of the compounds not comprising this symmetry around Z is very frequently excellent.

As has been mentioned above, when said hydrocarbon-based radicals $R_1$, $R_2$, $R_3$, $R_4$, $R_5$ and $R_6$ are linked via a carbon to the atoms Pn, this carbon atom may be of $sp^3$ aliphatic hybridization, or of $sp^2$ hybridization, ie especially of aromatic nature on account of the instability of the vinyl groups. Links with atoms of aromatic nature are preferred. Another kind of link is preferred, which is the link via the nitrogen atom of an amine function or of an imine function.

Thus, it is desirable for at least 3, advantageously at least 4, preferably at least 5 and more preferably all of the radicals $R_1$, $R_2$, $R_3$, $R_4$, $R_5$ and $R_6$ to be linked to the Pn via an aromatic carbon atom and/or a nitrogen atom of a peralkylated amine or imine function.

When the peralkylated imines are phosphonimines, this results in several sequences of the type Pn=N=Pn with one common atom Pn; in this case, to ensure solubility in solvents when the molecule is symmetrical of order 4 (four identical substituents) around a phosphorus, it is preferable for there to be a number of carbon atoms greater by at least a third and advantageously by at least a half of the sum of the nitrogen and phosphorus atoms.

The counterions are advantageously chosen from sparingly nucleophilic anions and mixtures of anions $X^-$, ie, when they are single, they are such that XH has a pKa of not more than 3, advantageously 2, preferably 1 and more preferably zero, and when they consist of a mixture of anions, at least one of the anions is sparingly nucleophilic.

It should be mentioned, however, that the counterions corresponding to the superacids weaken the catalytic effect; thus, bromide is more effective than $BF_4^-$. Thus, wherever it is possible and when the catalysis needs to be strong, it is preferable to avoid counteranions that correspond to a high Hammett constant and thus to select anions corresponding to acids with a Hammett constant of not more than 12 and preferably 10.

According to one of the preferred embodiments of the invention, this use is implemented in a process that is useful for performing a nucleophilic substitution of $SN_{Ar}$ type on an aromatic substrate, characterized in that an aromatic substrate of general formula (III):

Ar-(Ξ)

in which Ar is an aromatic radical in which the nucleus bearing Ξ is electron-poor either because it comprises at least one hetero atom in its ring, or because the sum of the $\sigma_p$ of its substituents, besides the Ξ, is at least equal to 0.2, advantageously 0.4 and preferably 0.5; the substituents possibly being leaving groups capable of giving rise to a new substitution and thus of being noted Ξ, in a subsequent $SN_{Ar}$;

in which Ξ is a leaving group, advantageously in the form of an anion Ξ⁻;

is subjected to the action of a nucleophilic agent capable of exchanging with the or at least one of the substituents Ξ in the presence of a catalyst of formula (I).

It is desirable for the molar ratio between the catalyst and the nucleophilic agent used in the reaction to be at least equal to 0.1‰, advantageously 0.5‰, preferably 1‰ and more preferably 0.5%.

It is also desirable for the molar ratio between the catalyst and the substrate used in the reaction to be at least equal to 0.1‰, advantageously 0.5‰, preferably 1‰ and more preferably 0.5%.

Strictly speaking, there is no upper limit, but, unless the compound of formula II is used as the reagent that is the vector of $X^-$, which is then the nucleophile, it is more economical for the molar ratio between the catalyst and the nucleophilic agent used in the reaction to be not more than ⅓, advantageously ⅕ and preferably 10%.

Advantageously, Ξ⁻ is less nucleophilic than the nucleophilic agent with which it exchanges; since the nucleophilicity scales are difficult to use, a person skilled in the art may use the empirical rule that ΞH is advantageously more acidic than the nucleophile in protonated form. Ξ may be a nitro or quaternary ammonium group, but it is preferable for it to be a pseudohalogen group or, preferably, a halogen atom chosen from chlorine, bromine and iodine.

The term "pseudohalogen" is intended to denote a group whose loss leads to an oxygenated anion, the anionic charge being borne by the chalcogen atom, and whose acidity, expressed by the Hammett constant, is at least equal to that of acetic acid, advantageously to the second acidity of sulfuric acid and preferably to that of trifluoroacetic acid.

Illustrations of pseudohalogens of this type that may be mentioned in particular include the anions corresponding to sulfinic acid and sulfonic acid, which are advantageously perhalogenated on the sulfur-bearing carbon, and also carboxylic acids that are perfluorinated α to the carboxylic function.

Since the nucleophilic substitution reaction is relatively facilitated when Ξ represents an iodine atom, the process claimed is more particularly advantageous when Ξ symbolizes a chlorine or bromine atom or a pseudohalogen.

As regards the substituent(s) of Ar, occasionally referred to as "groups R", they are present on the aromatic nucleus, and are selected such that they induce an overall depletion of electrons on the nucleus that is sufficient to allow the activation of the substrate and the stabilization of the Meisenheimer complex (cf. indication given above).

The aromatic substrate thus substituted has an electron density at most equal to that of phenyl, advantageously at most in the region of that of a chlorophenyl and preferably of a difluorophenyl.

This depletion may also be due to the presence in the aromatic ring of a hetero atom such as, for example, in pyridine or quinoline. It is important to point out that this type of depletion is observed only when Ar symbolizes a compound with a 6-membered ring and the hetero atom belongs to column V (essentially nitrogen or phosphorus) as defined in the Periodic Table of the Elements published in the supplement to the Bulletin de la Société Chimique de France in January 1966.

Preferably, the group or at least one of the groups R is a non-leaving electron-withdrawing substituent and more preferably is other than a carbon-based substituent.

The substituent(s) R when they are withdrawing may be chosen from halogen atoms and the following groups:

$NO_2$ $SO_2Alk$ and $SO_3Alk$

Rf and preferably $CF_3$

CN

CHO

COAlk

COΞ', in which Ξ' is chosen from the same values as Ξ, with the same preferences COOAlk phosphone and phosphonate with the symbol Alk representing a hydrogen or, advantageously, a linear or branched, preferably $C_1$ to $C_4$ alkyl group.

Examples of preferred groups R that may be mentioned more particularly include halogen atoms and the nitro group.

The electron-withdrawing substituent(s) R is (are) more preferably located in an ortho and/or para position relative to the leaving group(s) Ξ.

As regards the nucleophilic agent intended to replace the leaving group(s) X on the aromatic substrate, it may be generated in situ during the irradiation reaction.

As nucleophilic agents that may be used according to the invention, mention may be made especially of:

phosphine, arsine and ammonia, phosphines, arsines and amines, and anions thereof, water and its anion, alcohols and alkoxides, hydrazines and semicarbazides, salts of weak acids such as carboxylates, thiolates, thiols and carbonates, cyanide and its salts, malonic derivatives, and imines.

The nitrogenous nucleophilic derivatives are of most particular advantage in the context of the claimed process.

Nucleophilic agents whose nucleophilic function is an anion give good results.

Another aim of the present invention is to provide a process that is especially useful for performing exchange reactions between fluorine and halogens with a higher atomic number present on the aromatic substrate, and especially exchange reactions between fluorine and chlorine.

Reverse exchange reactions, ie the replacement of one halogen with a halogen of a higher row, are also possible. However, this type of reaction is less advantageous and is also more difficult to perform. Nevertheless, it is within the capability of a person skilled in the art to exploit the teaching of the present process to perform other exchange reactions, and especially these reverse exchange reactions.

In the case of exchange reactions between fluorine and halogens with a higher atomic number, the use of a fluoride as nucleophilic agent is preferred.

Advantageously, the fluoride is a fluoride of an alkali metal with an atomic number at least equal to that of sodium, and is preferably a potassium fluoride.

The alkali metal or alkaline-earth metal fluoride is at least partially present in the form of a solid phase.

In general, the reaction is performed at a temperature below that selected for a reaction performed with a common catalyst (the ultimate example of which is tetramethylammonium).

The reaction is generally performed in a solvent and, in this case, it is preferable to perform the reaction at a temperature at least 10° C., advantageously 20° C. and preferably 40° C. below the limit temperature usually accepted for said solvent used.

A continuous recovery of the most volatile compounds may also be performed gradually as they are formed. This recovery may be performed, for example, by distillation.

According to one of the possible embodiments, the heating is performed partially or totally by microwaves of the present invention; in this case, it is preferable for the microwaves to be emitted over short periods (from 10 seconds to 15 minutes) alternating with phases of cooling. The respective durations of the microwave emission periods and of the cooling periods are chosen such that the temperature at the end of each microwave emission period remains below an initial set temperature, which is generally less than the resistance temperature of the ingredients of the reaction mixture.

It is also possible to perform such a heating according to a procedure in which the reaction mixture is simultaneously subjected to microwaves and to cooling. According to this variant, the power released by the microwaves is then chosen such that, for an initial set temperature which is generally the working temperature, it is equivalent to the energy removed by the cooling system, plus or minus the heat evolved or absorbed by the reaction.

Such an actinic heating process moreover has the advantage of being compatible with a continuous functioning mode. This mode of use advantageously makes it possible to surmount the heat exchange problems that may arise during the operations of opening and closing of the reactor in which the microwaves are emitted.

According to this mode of functioning, the materials to be activated are introduced continuously via an inlet orifice into the reactor, where they undergo an activation by microwaves and the activated products are removed continuously from said reactor via an outlet orifice.

In the case of actinic heating by microwave, it is recommended to use a power evolved by the microwaves of between 1 and 50 watts per milliequivalent of aromatic substrate. It is also desirable to accept the constraint according to which the power evolved by the microwaves is between 2 and 100 watts per gram of reaction mixture.

The catalyst according to the invention may be used concomitantly with a catalyst acknowledged as being a phase-transfer catalyst, especially when this catalyst is a catalyst of cationic nature.

Such a concomitant use is all the more appropriate since the mechanism of action appears to be different.

The best phase-transfer catalysts that may be used are generally oniums, ie they are organic cations whose charge is borne by a metalloid. Among the oniums that may be mentioned are ammoniums, phosphoniums and sulfoniums. However, other phase-transfer catalysts may also be used provided that the phase-transfer catalysts are positively charged. They may also be cryptand cations, for example alkali-metal-cryptand crown ethers.

These phase-transfer catalysts may be used in the presence or absence, preferably in the presence, of an alkali metal cation that is particularly heavy and thus from a high atomic row, such as cesium and rubidium.

When the present invention is used to carry out a chlorine/fluorine exchange reaction, a dipolar aprotic solvent, a solid phase consisting at least partially of alkali metal fluorides and a reaction-promoting cation are generally used, said cation being a heavy alkali metal or an organic phase-transfer agent, this agent being of cationic nature.

The content of alkali metal cation, when it is used as promoter, is advantageously between 1 mol % and 5 mol % and preferably between 2 mol % and 3 mol % of the nucleophilic agent used. These ranges are closed ranges, ie they include their limits.

The reagent may comprise, as promoter, phase-transfer agents that are oniums (organic cations whose name ends with onium). The oniums in general represent 1 mol % to 10 mol % and preferably from 2 mol % to 5 mol % of the aromatic substrate, and the counterion may be of any nature but is usually halogenated.

Among the oniums, the preferred reagents are tetraalkylammoniums of 4 to 28 carbon atoms and preferably from 4 to 16 carbon atoms. The tetraalkylammonium is generally tetramethylammonium.

Phosphoniums and especially phenylphosphoniums should also be mentioned, which have the advantage of being stable and relatively sparingly hygroscopic; however, these reagents are relatively expensive.

The aprotic solvent of halex type advantageously has a significant dipolar moment. Thus, its relative dielectric constant epsilon is advantageously at least equal to about 10; preferably, the epsilon is less than or equal to 100 and greater than or equal to 25.

It has been possible to show that the best results were obtained when dipolar aprotic solvents with a donor index of between 10 and 50 were used, said donor index being the $\Delta H$ (enthalpy variation) expressed in kilocalories of the combination of said dipolar aprotic solvent with antimony pentachloride.

The oniums are chosen from the group of cations formed by columns VB and VIB as defined in the Periodic Table of the Elements published in the supplement to the Bulletin de la Société Chimique de France in January 1966, with four or three hydrocarbon-based chains, respectively.

In general, it is known that a fine particle size has an influence on the kinetics. Thus, it is desirable for said solid in suspension to have a particle size such that its $d_{90}$ (defined as the mesh that allows 90% by mass of the solid to pass through) is not more than 100 μm, advantageously not more than 50 μm and preferably not more than 200 μm. The lower limit is advantageously characterized in that the $d_{10}$ of said solid in suspension is not less than 0.1 μm and preferably not less than 1 μm.

In general, the ratio between said nucleophilic agent, preferably the alkali metal fluoride, and said substrate is between 1 and 1.5 and preferably in the region of 5/4 relative to the exchange stoichiometry.

The mass content of solids present in the reaction medium is advantageously not less than 1/5, advantageously 1/4 and preferably 1/3.

The stirring is advantageously performed such that at least 80% and preferably at least 90% of the solids are maintained in suspension by the stirring.

According to the present invention, the reaction is advantageously performed at a temperature ranging from about 150 to about 250° C. In the present description, the term "about" is used to illustrate the fact that the values that follow it correspond to mathematic round-ups and especially that, in the absence of a decimal point, when the figure(s) the furthest to the right in a number are zeros, these zeros are positional zeros rather than significant figures, except, of course, if otherwise specified.

However, it should be pointed out that when the temperature increases, the kinetics increase but the selectivity decreases.

Another aim of the present invention is to provide a composition capable of serving as a reagent for nucleophilic substitution, especially aromatic nucleophilic substitution.

This aim is achieved by means of a composition comprising:

a polar aprotic solvent;
a nucleophile;
a compound of formula (I).

It should be noted that the compounds of formulae (I) and (II) are particularly suitable for the usual recycling techniques.

Another aim of the invention is to provide, besides that of having provided a novel family of novel compounds that is useful as nucleophilic substitution catalysts having a pronounced catalytic nature.

Another aim of the present invention is to provide a process for synthesizing compounds that are used or that may be used as catalysts for second order nucleophilic substitution and especially for $SN_{Ar}$ nucleophilic substitution.

These aims have been achieved with compounds of formula (I) in which the number of alkyl substituents is not more than 2 and in which the total number of carbons is not less than 14 and preferably 16 per positive charge borne by the molecule. It should also be pointed out that it is particularly advantageous to have molecules that are not completely symmetrical around one of the atoms Z, but also around one of the atoms Pn.

Thus, it may be indicated that the sum of the carbons in the radicals $R_1$, $R_2$, $R_3$, $R_4$, $R_5$ and $R_6$ is greater than 12, preferably not less than 14 and advantageously not less than 16.

The condition regarding the alkyls may also be expressed by indicating that not more than 2 and preferably not more than one of the radicals $R_1$, $R_2$ and $R_3$, on the one hand, and/or $R_4$, $R_5$ and $R_6$, on the other hand, represent an alkyl group.

Finally, when symmetry is not desired, the absence of symmetry relative to Z may be expressed by indicating that the combination consisting of $R_1$, $R_2$ and $R_3$ must be different, for at least one of these components, than the combination $R_4$, $R_5$ and $R_6$. As regards the non-symmetry around one of the Pn when it is desired, this absence of symmetry may be expressed in the following manner: at least one of the radicals $R_4$, $R_5$ and $R_6$ must be different than the radical consisting of $(R_1)$ $(R_2)$ $(R_3)Pn=N-$.

The limitation regarding the number of alkyl derivatives is linked to the fact that, according to the present invention, it has been shown that it was desirable for the substituents $R_1$ to $R_6$ especially to have a donor nature via a mesomeric effect, so as to delocalize the positive charge better. However, alkyl chains with a carbon number of greater than 5 may be advantageous for the compatibility of the catalyst with solvents of sparingly polar nature, ie solvents that are not miscible in all proportions with water.

According to the present invention, the targeted compounds may be synthesized by the action of an iminoid of formula $(R_1)$ $(R_2)$ $(R_3)P_n=ZH$ or derivatives thereof on suitable substrates, namely trivalent Pn compounds.

According to one of the modes of preparation, the iminoid in hydrogenated form or in the form of a salt, advantageously an alkali metal salt, is reacted with a trivalent Pn derivative [halogen>Pn—X in which X represents a leaving group] bearing a leaving group, advantageously halogen (preferably bromine or chlorine) the iminoid anion replaces the leaving group giving a sequence Pn=Z—Pn<. The final product may be obtained by quaternizing the Pn that has remained trivalent using a compound chosen from $R_4$—X', $R_5$—X' and $R_6$—X', in which X' is a leaving group, advantageously a halogen, preferably from a row at least equal to that of chlorine; and especially bromine and iodine.

The reaction may be written in the manner below:

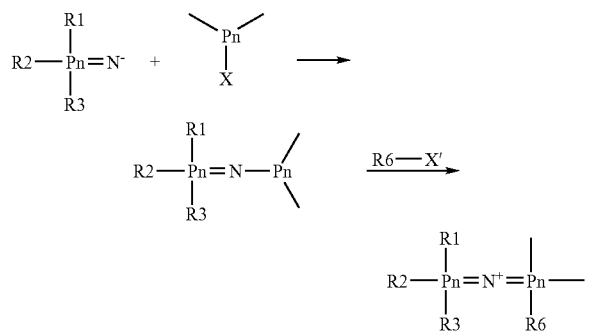

The quaternization reaction takes place at the end, and reactions to introduce the radicals $R_4$ and $R_5$ may take place in between.

For example, several iminoid groups may be grafted:

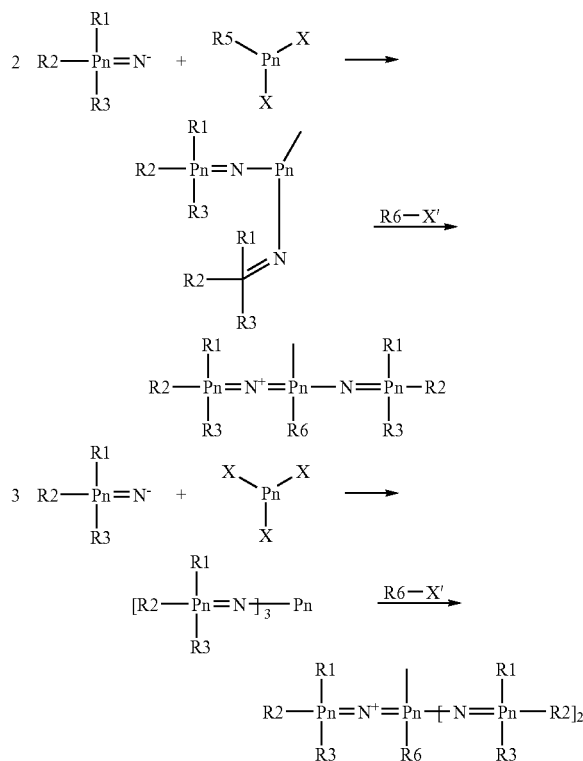

Usually, in this route, the iminoid is condensed with a phosphine already bearing two final substituents, in this case $R_4$ and $R_5$.

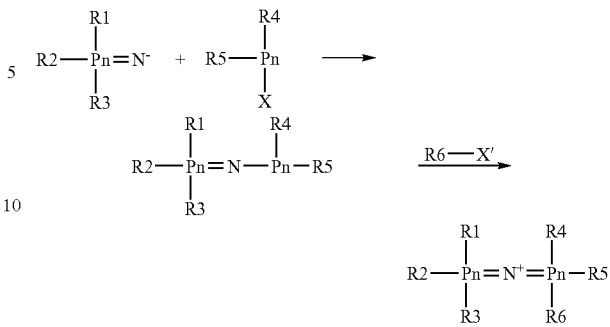

In this case also, one of the Pn, preferably both of them, is (are) advantageously P.

Z is advantageously nitrogen.

According to another mode of action, the anion of the iminoid is converted into a cation by oxidation, advantageously using a positive halogen (commonly written in the case of bromine as $Br^+$) or a molecular halogen, usually bromine, and is placed in contact with a trisubstituted Pn $(R_4)(R_5)(R_6)$Pn; thus directly giving a compound according to the present invention. This technique is developed further:

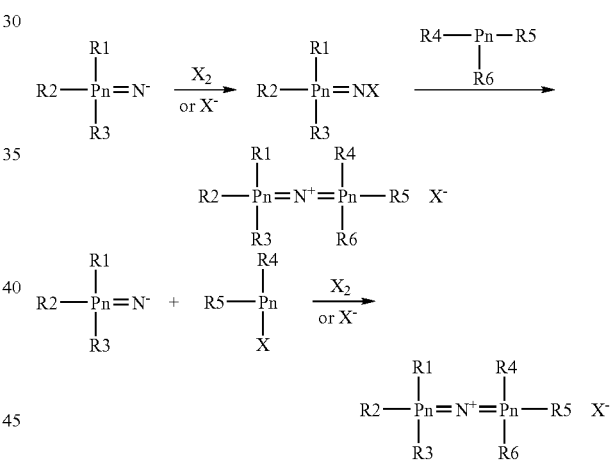

In this case also, one of the Pn, and preferably both of them, is (are) advantageously P.

Z is advantageously nitrogen.

The reactivity and the polyvalency of $(R_1)(R_2)(R_3)$PN=ZH, and of the alkali metal salts thereof (where appropriate in the presence of molecular halogen, usually bromine) and especially those of $(R_1)(R_2)(R_3)$P=NLi makes it possible to perform many catalyst syntheses, whether or not the molecules are already known. Its use constitutes an advantageous route of access for the compounds used as catalyst in the present invention. The reactions in the examples below are typical examples thereof.

According to another embodiment of the present invention, the synthesis may be performed by reacting a trisubstituted phosphinimine compound with a halophosphonium halide, which phosphonium bears three hydrocarbon-based substituents. The halophosphonium halide:

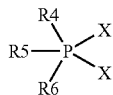

may be produced in situ by the action of a halide on a phosphine. The reaction may be written as below, in which the condensation example taken is the condensation of a phosphinimine with a triphenylphosphine in the presence of bromine.

In this case, the synthesis of the phosphiniminophosphonium bromide may be performed by reacting phosphinimines with dibromophosphoranes corresponding to the desired salt. The phosphinimines are obtained by deprotonating the corresponding aminophosphonium salt in the presence of a strong base such as sodium amide.

The reaction may be written as below:

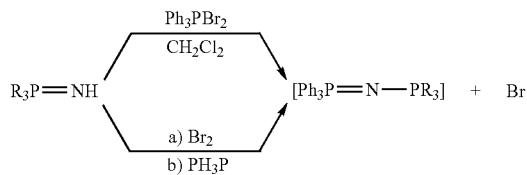

In this equation, the radicals R' may correspond, for example, to $R_1$, $R_2$ and $R_3$, and the radicals R may correspond to $R_4$, $R_5$ and $R_6$, or vice versa.

As regards the procedure, two options are possible, one reacting the phosphinimine with the preformed dibromophosphorane, another reacting this same phosphinimine with bromine and then with the appropriate phosphine.

Needless to say, the technique is performed under an atmosphere of dry inert gas. The starting phosphonimines are generally obtained by the action of one equivalent of N-butyllithium as base on an aminophosphonium halide, generally the bromide. Certain phosphinimines are commercially available. Dibromophosphorane is prepared beforehand by simple addition of a stoichiometric amount of dibromine to the appropriate phosphine. As indicated in the typical equation below:

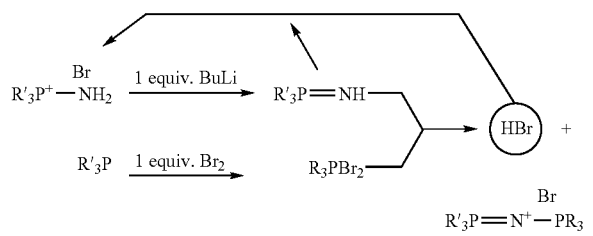

In this equation, the radicals R' may correspond, for example, to $R_1$, $R_2$ and $R_3$, and the radicals R may correspond to $R_4$, $R_5$ and $R_6$, or vice versa.

According to one variant already mentioned above of the present invention, the synthesis of these symmetrical or dyssymmetrical compounds is performed using an intermediate known as a phosphonium azayldiide. This reaction may be represented schematically as below, it being understood, of course, that, in this example, the phenyls may be replaced with $R_1$, $R_2$, $R_3$ and $Ar_3$ may be replaced with $R_4$, $R_5$ and $R_6$.

Equation No. 3

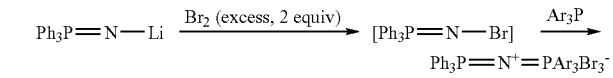

The method described [lacuna] to gain access to tribromo derivatives. By using only one equivalent of bromine (instead of 2), the monobromo salts are synthesized directly.

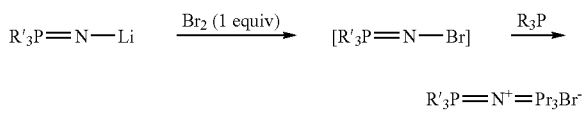

In this equation, the radicals R' may correspond, for example, to $R_1$, $R_2$ and $R_3$, and the radicals R may correspond to $R_4$, $R_5$ and $R_6$, or vice versa.

This simple method makes it possible to obtain, in the same reaction medium ($R_3$PNLi is prepared in situ by the action of 2 equivalents of BuLi on the corresponding aminophosphonium salt) the desired phosphiniminophosphonium salts under very mild conditions and very quickly.

Needless to say, salts other than the lithium salts may be used, but the lithium salt is the easiest to manufacture using butyllithium. The reactions are performed in common solvents, generally in optionally cyclic ethers, for instance THF, or chlorinated derivatives, for instance dichloromethane, the temperature usually used being between −30° C. and room temperature, more generally between −20° C. and room temperature.

Figure 1:
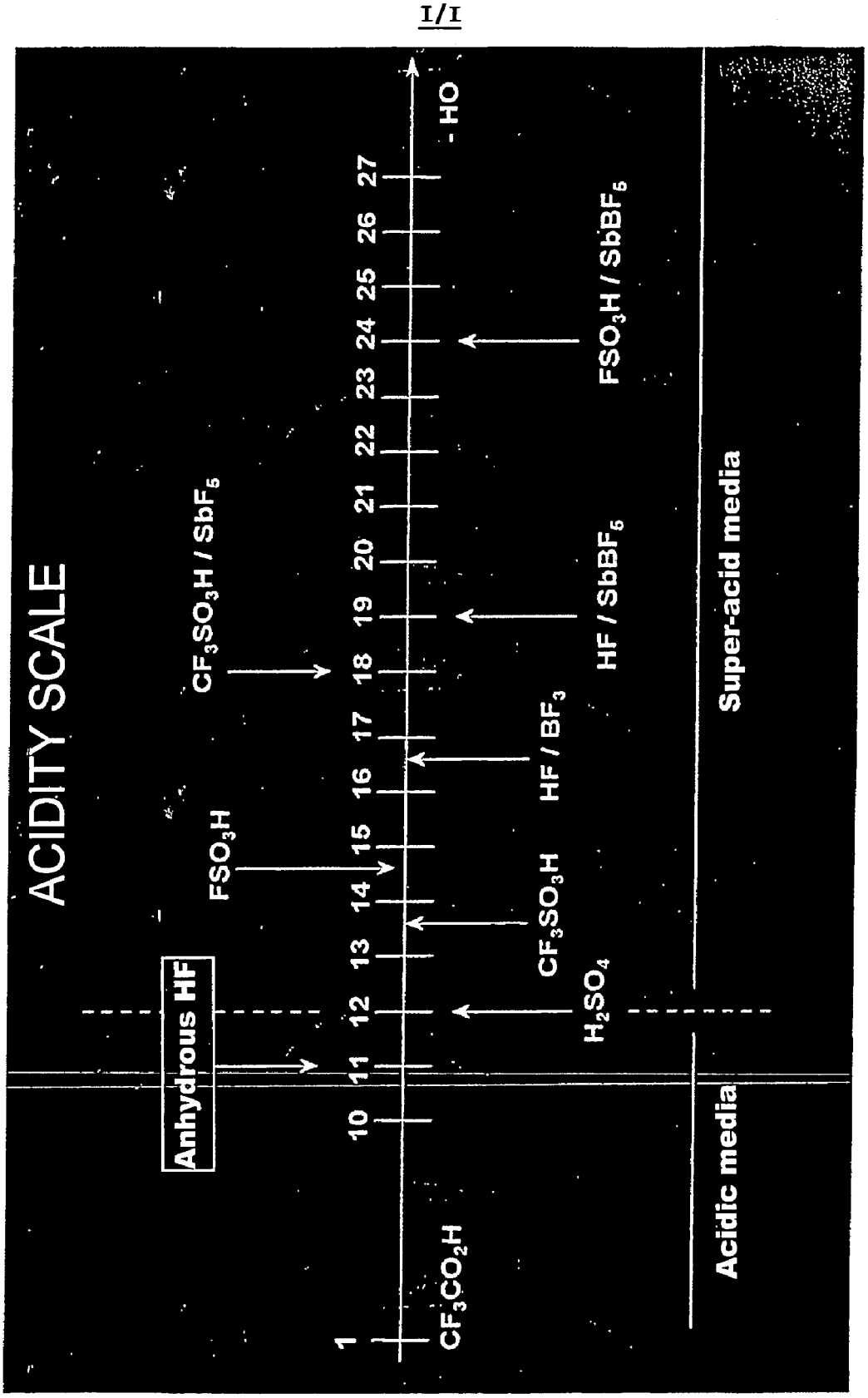
FIG. 1 is a chart of the acidity scale of acidic and super acidic media in pKa values.

The examples that follow are given as non-limiting illustrations of the invention:

EXAMPLE 1

Preparation of 4-fluoronitrobenzene Comparison with "Already-Known Catalysts"

Procedure

The following are introduced into a 60 ml tube:
para-chloronitrobenzene
DMSO
the catalyst
KF.

The tubes are closed with a septum and a screw stopper, and then heated with stirring for 4 hours at 150° C. After cooling to room temperature, about 10 g of water are added, followed by 5 g of dichloromethane, and, after settling of the phases and separation of the organic and aqueous phases, the aqueous phase is back-extracted twice with 5 g of dichloromethane. The various organic phases are combined and analyzed by GC.

Charge table

| Test | PCNB mass (g) | KF mass (g) | KF equivalent/ pCNB | DMSO mass (g) | Catalyst nature | Catalyst mass (g) | Catalyst equivalent/ pCNB |
|---|---|---|---|---|---|---|---|
| A | 5.0087 | 2.03 | 1.10 | 5 |  | 0 | 0 |
| B | 5.0062 | 2.03 | 1.10 | 5 | TMAC | 0.1086 | 0.031 |
| C | 5.0048 | 2.03 | 1.10 | 5 | Bu$_4$PBr | 0.3237 | 0.030 |
| D | 5.0049 | 2.04 | 1.11 | 5 | Tetrakis | 0.381 | 0.030 |
| E | 5.0089 | 2.03 | 1.10 | 5 | Ph$_4$PBr | 0.4002 | 0.030 |
| F | 5.004 | 2.03 | 1.10 | 5 | PPNCl | 0.548 | 0.030 |

TMAC = tetramethylammonium chloride
Bu$_4$PBr = tetrabutylphosphonium bromide
tetrakis = tetrakis(diethylamino)phosphonium bromide
Ph$_4$PBr = tetraphenylphosphonium bromide
PPNCl = bis(triphenylphosphoranylidene)ammonium chloride of formula:

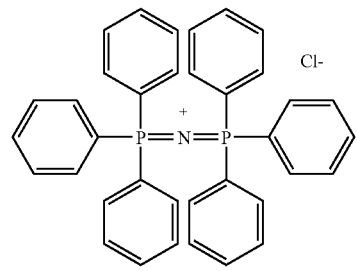

Results

| Test | Catalyst nature | Degree of conversion of the pCNB | Yield of PFNB |
|---|---|---|---|
| A |  | 7 | 4 |
| B | TMAC | 46 | 46 |
| C | Bu$_4$PBr | 15 | 15 |
| D | Tetrakis | 17 | 17 |
| E | Ph$_4$PBr | 11 | 6 |
| F (according to the invention) | PPNCl | 62 | 62 |

It is noted that the catalyst according to the invention is by far the best catalyst, as regards both the reaction selectivity and the degree of conversion.

EXAMPLE 2

Preparation of 2,4-difluoronitrobenzene:
Comparison with "Already-Known Catalysts"

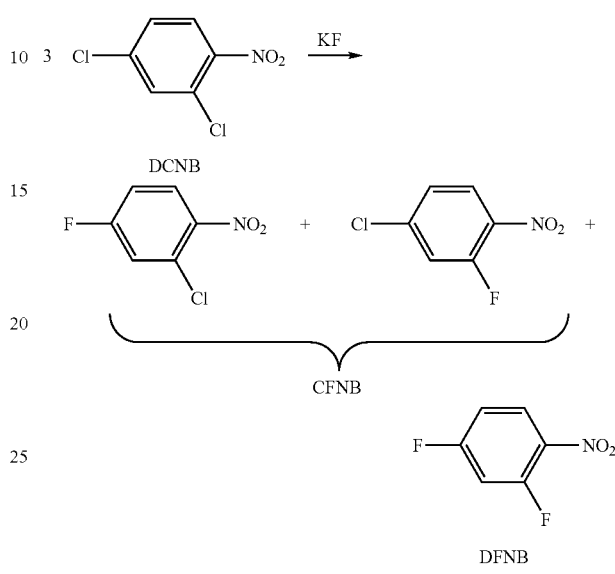

Procedure

The following are introduced into a 60 ml tube:

2,4-dichloronitrobenzene sulfolane the catalyst

KF.

The tubes are closed with a septum and screw stopper, and are then heated with stirring for 4 hours at 170° C. After cooling to room temperature, about 10 g of water are added, followed by 5 g of dichloromethane, and, after settling of the phases and separation of the organic and aqueous phases, the aqueous phase is back-extracted twice with 5 g of dichloromethane. The various organic phases are combined and analyzed by GC.

Charge table

| Test | DCNB mass (g) | KF mass (g) | KF equivalent/ DCNB | Sulfolane mass (g) | Catalyst nature | Catalyst mass (g) | Catalysts equivalent/ DCNB |
|---|---|---|---|---|---|---|---|
| A | 5.0062 | 3.33 | 2.2 | 6.3 |  | 0 | 0 |
| B | 5.0026 | 3.34 | 2.2 | 6.3 | TMAC | 0.0868 | 0.031 |
| C | 5.0084 | 3.33 | 2.2 | 6.3 | Bu$_4$PBr | 0.266 | 0.030 |
| D | 5.0149 | 3.34 | 2.2 | 6.3 | Tetrakis | 0.312 | 0.030 |
| E | 5.0066 | 3.34 | 2.2 | 6.3 | Ph$_4$PBr | 0.358 | 0.030 |
| F | 5.0092 | 3.34 | 2.2 | 6.3 | PPNCl | 0.449 | 0.030 |

TMAC = tetramethylammonium chloride
Bu$_4$PBr = tetrabutylphosphonium bromide
tetrakis = tetrakis(diethylamino)phosphonium bromide
Ph$_4$PBr = tetraphenylphosphonium bromide
PPNCl = bis(triphenylphosphoranylidene)ammonium chloride.

Results

| Test | Catalyst nature | Degree of conversion of the DCNB | Yield of CFNB | Yield of DFNB |
|---|---|---|---|---|
| A |  | 25 | 20 | 2 |
| B | TMAC | 97 | 29 | 68 |
| C | Bu$_4$PBr | 95 | 27 | 67 |
| D | Tetrakis | 96 | 24 | 69 |
| E | Ph$_4$PBr | 92 | 31 | 60 |
| F | PPNCl | 98 | 16 | 77.5 |

The catalyst according to the invention [lacuna] which gives both the best degree of conversion, but also the one which gives the best yield of difluoro product.

EXAMPLE 3

Preparation of 1-fluoro-3,5-dichlorobenzene and 1,3-difluoro-5-chlorobenzene: Examples for Comparison with "Already-Known Catalysts"

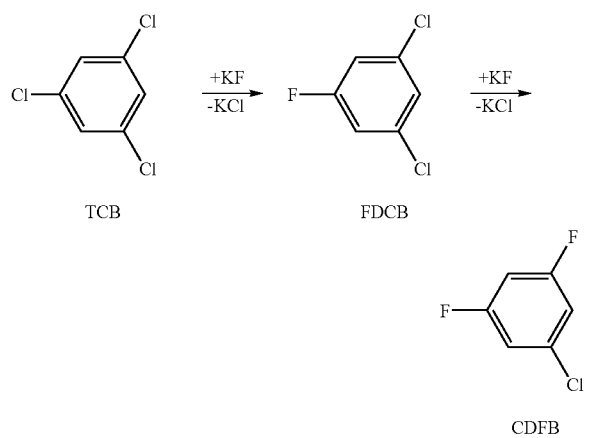

Procedure

The following are introduced into a 60 ml tube:
1,3,5-trichlorobenzene
sulfolane
the catalyst
KF.

The tubes are closed with a septum and screw stopper, and are then heated with stirring at 210° C. for the time indicated in the table. After cooling to room temperature, about 10 g of water are added, followed by 5 g of dichloromethane, and, after settling of the phases and separation of the organic and aqueous phases, the aqueous phase is back-extracted twice with 5 g of dichloromethane. The various organic phases are combined and analyzed by GC.

Results

| Test | Catalyst nature | Degree of conversion of the TCB (%) | Yield of FDCB | Yield of CDFB |
|---|---|---|---|---|
| A | Bu$_4$PBr | 3 | 2.5 | 0 |
| B | Bu$_4$PBr | 3 | 2.7 | 0 |
| C | Tetrakis | 3 | 2.9 | 0 |
| D | PPNCl | 23 | 21 | 0.7 |

The catalyst according to the invention is on the one hand the one that gave the highest degree of conversion, but on the other hand the only one that gave a small amount of difluorination.

EXAMPLE 4

Preparation of 4-fluoronitrobenzene

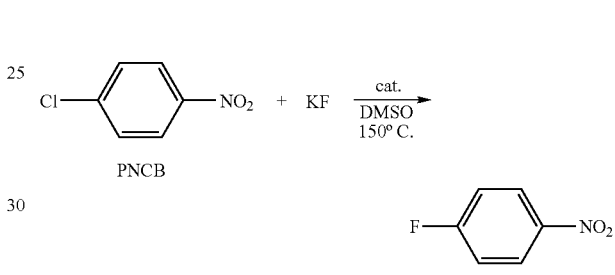

Procedure

The following are introduced in order into a 30 ml Schott tube:
4-chloronitrobenzene
the catalyst
KF
DMSO.

The tubes are closed with a septum and screw stopper, and are then heated with stirring for 3 hours at 150° C. After cooling to room temperature, about 10 g of water are added, followed by 5 g of dichloromethane, then 5 g of dichloromethane again, and, after settling of the phases and separation of the organic and aqueous phases, the aqueous phase is back-extracted twice with 5 g of dichloromethane. The various organic phases are combined and analyzed by HPLC.

Charge table

| Test | T (h) | TCB mass (g) | KF mass (g) | KF equivalent/ TCB | Sulfolane mass (g) | Catalyst nature | Catalyst mass (g) | Catalysts equivalent/ TCB |
|---|---|---|---|---|---|---|---|---|
| A | 3 | 1.508 | 0.96 | 2 | 2 | Bu$_4$PBr | 0.055 | 0.02 |
| B | 3 | 1.506 | 0.97 | 2 | 2 | Bu$_4$PBr | 0.143 | 0.05 |
| C | 2 | 1.503 | 0.97 | 2 | 2 | Tetrakis | 0.099 | 0.03 |
| D | 2 | 1.505 | 0.97 | 2 | 2 | PPNCl | 0.143 | 0.03 |

Charge table

| Test | Mass PNCB g | eq Kf to PNCB | eq DMSO to PNCB | catalyst nature | mass in g catalyst | eq cat. to PNCB |
|---|---|---|---|---|---|---|
| 1 | 2.0092 | 1.11 | 3.00 | Nothing | 0 | 0 |
| 2 | 2.0493 | 1.10 | 3.00 | [(CH$_3$)$_2$N]$_3$PNP[N(CH$_3$)$_2$]$_3$, BF$_4$- | 0.2261 | 0.041 |
| 3 | 2.1034 | 1.10 | 3.03 | [(CH$_3$)$_2$N]$_3$PNPBu$_3$, Br$^-$ | 0.2495 | 0.041 |
| 4 | 2.0962 | 1.10 | 3.00 | Ph$_3$PNPBu$_3$, Br$^-$ | 0.2982 | 0.040 |
| 5 | 2.0111 | 1.13 | 3.01 | [(CH$_3$)$_2$N]$_3$PNP[N(CH$_3$)$_2$]$_3$, Br$^-$ | 0.2186 | 0.041 |
| 6 | 1.5620 | 1.09 | 3.23 | Ph$_3$PNP-[N(CH$_3$)$_2$]$_3$, Br$^-$ | 0.1871 | 0.043 |
| 7 | 1.5136 | 1.11 | 3.22 | Ph$_3$PNP((o)-MeOPh)$_3$, Br$^-$ | 0.2731 | 0.040 |
| 8 | 1.5069 | 1.13 | 3.24 | Bu3PNPBu$_3$, Br$^-$ | 0.1992 | 0.042 |

Ph$_3$PNP(Co)-MeOPh)$_3$, Br$^-$ —

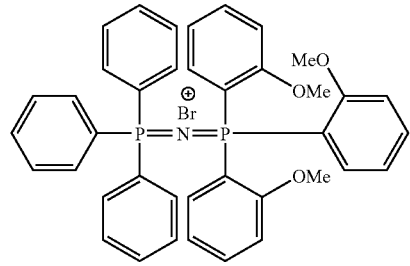

Results

| Test | Catalysts | Yield of PNFB |
|---|---|---|
| 1 | Nothing | 5.87% |
| 2 | [(CH$_3$)$_2$N]$_3$PNP[N(CH$_3$)$_2$]$_3$, BF$_4$- | 10.60% |
| 3 | [(CH$_3$)$_2$N]$_3$PNPBu$_3$, Br— | 15.77% |
| 4 | Ph$_3$PNPBu$_3$, Br— | 28.00% |
| 5 | [(CH$_3$)$_2$N]$_3$PNP[N(CH$_3$)$_2$]$_3$, Br— | 20.04% |
| 6 | Ph$_3$PNP[N(CH$_3$)$_2$]$_3$, Br— | 45.50% |
| 7 | Ph$_3$PNP((o)—MeOPh)$_3$, Br- | 37.82% |
| 8 | Bu$_3$PNPBu$_3$, Br— | 41.83% |

EXAMPLE 5

Preparation of 1,3,5-trifluorobenzene

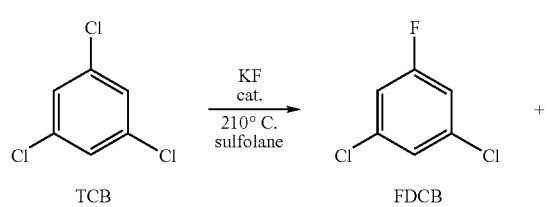

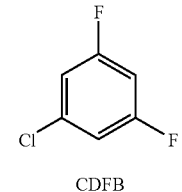

Procedure

The following are introduced in order into a 30 ml Schott tube:
1,3,5-trichlorobenzene
the catalyst
KF
sulfolane.

The tubes are closed with a septum and screw stopper, and are then heated with stirring for 3 hours at 210° C. After cooling to room temperature, about 10 g of water are added, followed by 5 g of dichloromethane, then 5 g of dichloromethane again, and, after settling of the phases and separation of the organic and aqueous phases, the aqueous phase is back-extracted twice with 5 g of dichloromethane. The various organic phases are combined and analyzed by GC.

Charge table

| Test | Mass TCB g | eq Kf to TCB | eq sulfolane to TCB | Catalyst nature | Mass in g of catalysts | eq cat. to TCB |
|---|---|---|---|---|---|---|
| 1 | 1.541 | 2.07 | 2.25 | Nothing | 0 | 0 |
| 2 | 1.5030 | 2.08 | 2.02 | [(CH$_3$)$_2$N]$_3$PNPBu$_3$, Br$^-$ | 0.1579 | 0.041 |
| 3 | 1.5076 | 2.01 | 2.03 | Ph$_3$PNPBu$_3$, Br— | 0.1860 | 0.040 |
| 4 | 1.5095 | 1.99 | 2.02 | [(CH$_3$)$_2$N]$_3$PNP[N(CH$_3$)$_2$]$_3$, Br— | 0.1408 | 0.040 |
| 5 | 1.4929 | 1.99 | 2.09 | Ph$_3$PNP[N(CH$_3$)$_2$]$_3$, Br— | 0.1767 | 0.049 |
| 6 | 1.0082 | 2.08 | 2.29 | Bu$_3$PNPBu$_3$, Br— | 0.1616 | 0.058 |

Results

| Test | Catalysts | RY DCFB | RY DFCB |
|---|---|---|---|
| 1 | Nothing | <0.5% | <0.5% |
| 2 | [(CH$_3$)$_2$N]$_3$PNPBu$_3$, Br | 25.39% | 1.04% |
| 3 | Ph$_3$PNPBu$_3$, Br— | 15.70% | 0.24% |
| 4 | [(CH$_3$)$_2$N]$_3$PNP[N(CH$_3$)$_2$]$_3$, Br— | 38.95% | 2.73% |
| 5 | Ph$_3$PNP[N(CH$_3$)$_2$]$_3$, Br— | 25.24% | 1.48% |
| 6 | Bu$_3$PNPBu$_3$, Br— | 11.55% | 1.28% |

Synthesis of Catalysts

The reactivity and polyvalency of $(R_1)(R_2)(R_3)$ Pn=ZH, and of the alkali metal salts thereof (where appropriate in the presence of molecular halogen, usually bromine) and especially those of $(R_1)(R_2)(R_3)$ P=NLi, makes it possible to perform numerous syntheses of catalysts, whether or not the molecules are already known. Its use constitutes an advantageous route of access for the compounds used as catalyst in the present invention. The reactions below are examples thereof.

EXAMPLE 6

Synthesis of Catalysts

The reaction of Ph$_3$P=NLi with PCl$_3$ leads quantitatively to the synthesis of the protonated triphosphinimine 3. The synthesis of this compound is performed by passing via the corresponding triphosphinimine(Ph$_3$P=N)$_3$P; this compound has a lone pair on the phosphorus atom, the electron density of which is considerably increased by the triple donor effect of the three Ph$_3$P=N— groups. This triphosphinimine then becomes basic enough to become protonated within a few minutes at 20° C., probably by attacking the protons of THF, and precipitating in this solvent in the form of the phosphonium salt [(Ph$_3$P=N)P—H]$^+$Cl$^-$.

This availability of the lone pair makes this compound an advantageous intermediate for subsequent quaternization and to form a compound according to the invention.

Procedure

Trichlorophosphine (1.4 mmol, 1 equivalent) is added by syringe in a single portion to a solution of Ph$_3$P=NLi (4.2 mmol, 3 equivalents) in 50 ml of THF at 20° C. The mixture is stirred at this temperature for 30 minutes; a white precipitate of N,N',N"-(phosphinio)tris-triphenylphosphinimine then forms in the medium. This precipitate is filtered off, rinsed with THF and obtained in pure form in a yield of 95%.

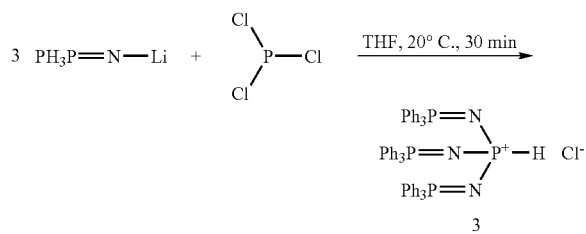

(Ph$_3$P=N)$_3$P is observed by $^{31}$P NMR after the action of n-butyllithium on a solution of the isolated salt 3 in dimethyl sulfoxide at 20° C. The triphosphinimine, which is very sensitive to moisture and to oxygen, could not be isolated. After deprotonation followed by addition of elemental sulfur, a mixture of the starting phosphonium salt (12%) and of oxidized triphosphinimine(Ph$_3$P=N)$_3$P=O (52%) and sulfurized triphosphinimine(Ph$_3$P=N)$_3$P=S (24%) is recovered.

The pKa of the [(Ph$_3$P=N)$_3$P—H]$^+$/(Ph$_3$P=N)$_3$P couple is between that of Ph$_3$=P=NH/Ph$_3$P=NLi and that of the n-butane/n-butyllithium couple, ie between 28 and 43.

EXAMPLE 7

Addition of one equivalent of chlorodiphenylphosphine to N-diphenylphosphinotriphenylphosphinimine 1, to give a phosphinimine containing a P=N—P—P sequence 2.

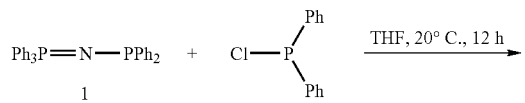

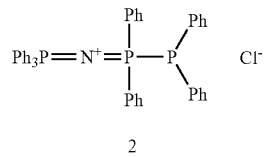

Ph$_2$PCl (4 mmol) is added dropwise at 20° C. to a solution of N-diphenylphosphinotriphenylphosphinimine (4 mmol) in THF. The solution is stirred for 12 hours at this temperature. Compound 2 precipitates over time. The solution is then filtered, the white solid collected is then recrystallized from acetonitrile and is obtained in a yield of 73%. Its structure is confirmed by melting point, mass spectrometry, $^{31}$P NMR and IR.

This compound has been described once in 1969 by Madersteig (Mardersteig, H. G.; Meinel, L.; Nöth, H. Z. Anorg. Allg. Chem. 1969, 368, 254–261 or Z. Anorg. Allg. Chem. 1970, 375, 272–280) starting with Ph$_3$P=NSiMe$_3$ and two equivalents of Ph$_2$PCl.

EXAMPLE 8

Synthesis of [Ph$_3$P=N=PBu$_3$]$^+$Br$^-$ 28 mmol of n-BuLi (as a commercial hexane solution: Aldrich) are added dropwise over about 15 minutes to a solution of 14 mmol of aminotriphenylphosphonium bromide in 125 ml of anhydrous THF, cooled to −15° C. The mixture is stirred constantly at this temperature for one hour (the diylide thus generated may be analyzed by phosphorus NMR, taking the precaution of performing the withdrawal under nitrogen). Under these conditions, 14 mmol (1 equivalent) of bromine predried by means of an acidic wash (36% H$_2$SO$_4$) are added. The reaction mixture is then stirred for 2 hours at a temperature of 0 to 5° C. 14 mmol of tributylphosphine are finally added to this solution. The mixture obtained is stirred constantly for about 12 hours (overnight).

The solution obtained is filtered and the filtrate is concentrated to dryness under reduced pressure. The $^{31}$P NMR analysis shows the majority presence of the expected product. The residue thus recovered is taken up in dichloromethane and washed with distilled water solution. The organic phase is dried over MgSO$_4$ and then concentrated to dryness. The product is redissolved in a minimum amount of dichloromethane and purified by adding a large volume of ether. The recovered product is subjected to ion exchange using a sodium iodide NaI solution in order to facilitate its purification [a]. After this treatment, the residue is taken up in 20 ml of ether and left under cold conditions (4° C.) for 3 hours. The iodinated product precipitates and is recovered in pure form by simple filtration.

The product in its brominated form will be obtained by simple ion exchange first using an AgNO$_3$ solution and then with an NaBr solution [b]. The oil obtained is left in the open air for several days in order to obtain a crystalline solid.

a) General Procedure for Purification by Exchanging Br$^-$ or Br$_3^-$ with I$^-$ The impure bromo residue recovered is taken up in dichloromethane and washed successively with 3 aqueous NaI solutions of concentration: (2.5 eq; 1.5 eq; 0.5 eq). The organic phase is then dried over MgSO$_4$ and concentrated to dryness in view of the various treatments.

b) General Procedure for Changing from I⁻ to Br⁻

The pure iodide obtained is redissolved in dichloromethane and washed with aqueous silver nitrate solution (2 eq). The organic phase is then washed with distilled water solution to remove the silver iodide residues in suspension. The organic phase then undergoes 3 washes with an aqueous NaBr solution (2.5 eq; 1.5 eq; 0.5 eq). The organic solution is finally dried over $MgSO_4$ and then concentrated to dryness under reduced pressure, thus allowing the pure bromo compound to be isolated.

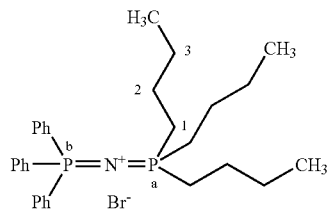

$C_{30}H_{42}BrNP_2$
558.520 g.mol⁻¹
Pale yellow solid
55% yield $^{31}P$ NMR (ppm) ($CDCl_3$): 41.14 (s, $^{(a)}P$; 17.28 (s, $^{(b)}P$)
$^1H$ NMR (ppm) ($CDCl_3$): 7.7–7.58 (m, 15H, aromatic); 1.98 (m, 6H, $^1CH_2$); 1.31 (m, 12H, $^2CH_2$—$^3CH_2$—); 0.79 (t, 9H, $CH_3$)
$^{13}C$ NMR (ppm) ($CDCl_3$): 133.18 (d, $J^4_{PC}$=2.83 Hz, $C_6H$, p-C); 131.31 (d, $J^3_{PC}$=11.16 Hz, $C_6H_5$ m-C); 128.14 (d, $J^2_{PC}$=13.01 Hz, $C_6H_5$ o-C); 128.14 (d, $J^2_{PC}$=13.01 Hz, $C_6H_5$ o-C); 127.69 (dd, $J^1_{PC}$=107.3 Hz, $J^3_{PaC}$=1.54 Hz, $C_6H_5$ ipso-C); 26.30 (d, $J^1_{PC}$=63.47 Hz, $CH_2$); 23.09 (d, $J^2_{PC}$=15.88 Hz, $CH_2$); 23.11 (d, $J^3_{PC}$=4.57 Hz, $CH_2$); 12.99 (s, $CH_3$)
Mass: FAB⁺ M—Br⁻; 478 [NBA matrix]
Microanalysis EXP.: C, 65.05%; H, 7.70%; P, 10.50%. THEO.: C, 64.45%; H, 7.51%; P, 11.10%; BR, 14.31%.

EXAMPLE 9

Synthesis of $[Ph_3P=N=P(o-C_6H_4OMe)_3]^+Br^-$ a) Synthesis of $[Ph_3P=N=P(o-C_6H_4OMe)_3]+Br_3^-$—

28 mmol of n-BuLi (as a commercial hexane solution: Aldrich) are added dropwise over about 15 minutes to a solution of 14 mmol of aminotriphenylphosphonium bromide in 125 ml of anhydrous THF, cooled to −15° C. The mixture is left under constant stirring at this temperature for one hour (the diylide thus generated may be analyzed by phosphorus NMR, taking the precaution to perform the withdrawal under nitrogen). Under these conditions, 35 mmol (2.5 equiv.) of a bromine solution predried by means of an acidic wash (36% $H_2SO_4$) are added. The reaction mixture is then stirred for 2 hours at a temperature of 0 to 5° C. 14 mmol of tri-o-anisylphosphine are finally added to this solution. The mixture obtained is left under constant stirring for about 12 hours (overnight).

The solution obtained is filtered and the precipitate is purified by simple washing, first with a solution of 30 ml of ethanol and then with a solution of 50 ml of ether. The tribromo salt of the expected product was obtained.

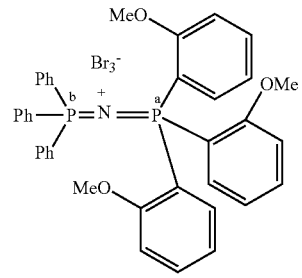

$C_{39}H_{36}Br_3NO_3P_2$
868.569 g.mol⁻¹
White solid
65% yield $^{31}P$ NMR (ppm) ($CH_2Cl_2$): 19.62 (d, $^{(a)}P$, $J^2_{PP}$=16.04 Hz); 15.06 (s, $^{(b)}P$), $J^2_{P-P}$=16.04 Hz)
$^1H$ NMR (ppm) ($CDCl_3$): 7.66–6.74 (m, 27H, aromatic); 3.16 (m, 9H, $OCH_3$)
$^{13}C$ NMR (ppm) ($CDCl_3$): 160.90 (d, $J^2_{PC}$=2.98 Hz, $C_6H_4$ o-C—OMe); 135.39 (d, Ar); 134.12 (d, Ani); 133.19 (d, Ani); 132.03 (d, Ar); 128.93 (d); 128.03 (dd, $J^1_{PC}$=111.27 Hz, $J^3_{PC}$=2.05 Hz, ipso-C—Ar); 121.13 (d, $J^3_{PC}$=13.77 Hz, Ani); 115.12 (dd, $J^1_{PC}$=116.50 Hz, $J^3_{PC}$=2.05 Hz, ipso-C-Anisyl); 111.97 (d, $J^3_{PC}$=7.07 Hz, Ani); 55.25 (s, OMe)
Mass: FAB⁺ M—Br⁻; 628 [NBA matrix]
Microanalysis EXP.: C, 53.19%; H, 4.13%; N, 1.72%. THEO.: C, 53.88%; H, 4.14%; N, 1.61%.

b) Reduction of the $Br_3^-$ to $Br^-$

The tribromo salts obtained are taken up in a dichloromethane solution and washed with aqueous sodium sulfite solution (2 eq). Decolorization of the organic phase is then rapidly observed, which is the characteristic sign of reduction of the trihalides. The organic phase is dried over $MgSO_4$ and then concentrated to dryness under reduced pressure. The phosphorus, proton and carbon spectra are good, but the microanalysis does not correspond either to the monobromo product or to the tribromo product.

c) Synthesis of $[Ph_3P=N=P(o-C_6H_4OMe)_3]^+Br^-$ 28 mmol of n-BuLi (as a commercial hexane solution: Aldrich) are added dropwise over about 15 minutes to a solution of 14 mmol of aminotriphenylphosphonium bromide in 125 ml of anhydrous THF, cooled to −15° C. The mixture is left under constant stirring at this temperature for one hour (the diylide thus generated may be analyzed by phosphorus NMR, taking care to perform the withdrawal under nitrogen). Under these conditions, 14 mmol (1 equivalent) of bromine predried by means of an acidic wash (36% $H_2SO_4$) are added. The reaction mixture is then stirred for 2 hours at a temperature of 0 to 5° C. 14 mmol of tri-o-anisylphosphine are finally added to this solution. The mixture obtained is left under constant stirring for about 12 hours (overnight). The solution obtained is filtered and the filtrate is concentrated to dryness under reduced pressure. The $^{31}P$ NMR analysis shows the majority presence of the expected product. The residue thus recovered is taken up in dichloromethane and washed with distilled water solution. The organic phase is dried over $MgSO_4$ and then concentrated to dryness. The product is redissolved in a minimum amount of dichloromethane and purified by adding a large volume of ether, from which it precipitates.

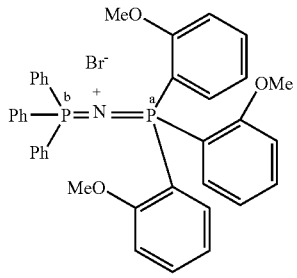

C$_{39}$H$_{36}$BrNO$_3$P$_2$
708.569 g.mol$^{-1}$
White solid
55% yield $^{31}$P NMR (ppm) (CH$_2$Cl$_2$): 20.17 (d, $^{(a)}$P, J$^2_{PP}$=16.15 Hz); 15.54 (s, $^{(b)}$P), J$^2_{P-P}$=16.15 Hz)

$^1$H NMR (ppm) (CDCl$_3$): 7.67–6.75 (m, 27H, aromatic); 3.19 (m, 9H, OCH$_3$) (ppm) (CDCl$_3$): δ4.9 ppm (s, OCH$_3$ Ani); 111.6 ppm (d, $^3$J$_{P-C}$=6.7 Hz, CH Ani); 114.8 ppm (d, $^3$J$_{P-C}$=112.1 Hz, C$_{IV}$ Ani); 120.8 ppm (d, $^3$J$_{PC}$=13.8 Hz, CH Ani); 127.1 ppm (d, $^1$J$_{PC}$=115.9 Hz, C$_{IV}$ Ph); 128.9 ppm (d, $^3$J$_{PC}$=13.4

$^{13}$C NMR Hz, CH Ph); 131.8 ppm (d, $^2$J$_{PC}$=11.5 Hz, CH Ph); 133.2 ppm (d, $^4$J$_{PC}$=2.06 Hz, CH Ph); 133.9 ppm (d, $^2$J$_{PC}$=10.05 Hz, CH Ani); 135.4 ppm (apparent s, $^4$J$_{PC}$≈0 Hz; CH Ani); 161.2 ppm (s, C—OMe Ani)

Mass: FAB$^+$ M—Br$^-$; 628 [NBA matrix]

Microanalysis EXP.: AWAITING THEO.: C, 66.11%; H, 5.12%; BR, 11.28%.

EXAMPLE 10

Synthesis of [(Me$_2$N)$_3$—P=N=P—(NMe$_2$)$_3$]$^+$Br$^-$

Comment: In this case, we used iminotris(dimethylamino) phosphorane [(CH$_3$)$_2$N]$_3$P=NH as starting substrate. Consequently, only one equivalent of n-BuLi is added to generate the corresponding azayldiide.

14 mmol of n-BuLi (as a commercial hexane solution: Aldrich) are added dropwise over about 15 minutes to a solution of 14 mmol of iminotris(dimethylamino)phosphorane [(CH$_3$)$_2$N]$_3$P=NH in 125 ml of anhydrous THF, cooled to −15° C. The mixture is left under constant stirring at this temperature for one hour (the diylide thus generated may be analyzed by phosphorus NMR, taking care to perform the withdrawal under nitrogen). Under these conditions, 14 mmol (1 equivalent) of bromine predried by means of an acidic wash (36% H$_2$SO$_4$) are added. The reaction mixture is then stirred for 2 hours at a temperature of 0 to 5° C. 14 mmol of tris(dimethylamino)phosphine are finally added to this solution. The mixture obtained is left under constant stirring for about 12 hours (overnight).

The reaction mixture is filtered and the precipitate containing the expected product is recovered. This product is taken up in a minimum amount of dichloromethane, to which are added a few drops of ethanol until the slight cloudiness has totally disappeared. The addition of a large volume of ether allows the majority of the impurities to be removed. The ether phase is then concentrated to dryness, taken up in ether and left at low temperature overnight. The product in monobromo form is recovered in pure form by simple filtration and the solid is dried over P$_2$O$_5$ overnight in a desiccator.

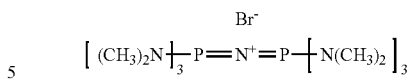

C$_{12}$H$_{36}$BrN$_7$P$_2$
420. 315 g.mol$^{-1}$
Beige-colored solid;

$^{31}$P NMR (ppm) (CDCl$_3$): 19.62 (s, 2P equivalent)
$^1$H NMR (ppm) (CDCl$_3$): 7.36–6.74 (t, 36H equivalent)
$^{13}$C NMR (ppm) (CDCl$_3$): 36.50 (t, J$^2_{PC}$=4.78 Hz) 2nd order system Mass: FAB$^+$ M—Br$^-$; 340 [NBA matrix]

Microanalysis EXP.: C, 34.29%; H, 8.64%; N, 23.00%; BR, 19.16%. THEO.: C, 34.26%; H, 8.51%; N, 23.31%; BR, 19.03%.

EXAMPLE 11

Synthesis of [(Me$_2$N)$_3$—P=N=PBu$_3$]$^+$Br$^-$ 14 mmol of a solution of dibromine diluted beforehand in 10 ml of dichloromethane at −5° C. are added dropwise to a solution of 14 mmol of tributylphosphine in 70 ml of anhydrous dichloromethane. The mixture is stirred for 1 hour at a temperature of 0 to −5° C. (in situ formation of Bu$_3$PBr$_2$).

After addition of 1.5 equivalents of triethylamine, 14 mmol of iminotris(dimethylamino)phosphorane [(CH$_3$)$_2$N]$_3$P=NH in 14 ml of THF are then added to the solution of dibromotributylphosphorane Bu$_3$PBr$_2$. The resulting mixture is stirred overnight at room temperature.

The solution obtained is evaporated to dryness under reduced pressure. The residue recovered is taken up in ether and then filtered off. The pasty, semi-solid product is taken up in dichloromethane and washed with distilled water solution. The organic phase is dried over MgSO$_4$, filtered and then concentrated to dryness. The product is then suspended in ether and left overnight at low temperature. The pasty solid contained in the ether phase is triturated in a bath of cold alcohol at −70° C. and the solution is filtered. The pure product is finally dried in a desiccator over P$_2$O$_5$.

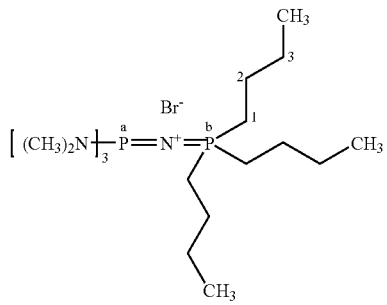

C$_{18}$H$_{45}$BrN$_4$P$_2$
459.432 g.mol$^{-1}$
Pale brown solid
48.8% yield $^{31}$P NMR (ppm) (CDCl$_3$): 29.62 (d, J$^2{}_{PP}$=30.65 Hz); 23.18 (d, J$^2{}_{PP}$=30.65 Hz)

$^1$H NMR (ppm) (CDCl$_3$): 2.6 (dd, 18H); 2 to 1.8 (m, $^1$CH$_2$, 6H); 1.55 to 1.3 (m, $^2$CH$_2$-$^3$CH$_2$, 12H); 0.87 (t, CH$_3$, 9H) (ppm) (CDCl$_3$): 36.76 (d, J$^2{}_{PC}$=4.47 Hz, MeN); 26.85 (dd, $^{13}$C NMR J$^1{}_{PC}$=66.24 Hz, J$^3{}_{PC}$=1.49 Hz, CH$_2$): 23.36 (d, J$^2{}_{PC}$=11.54 Hz, CH$_2$); 23.18 (s, CH$_2$CH$_3$); 13.20 (s, CH$_3$)

Mass: FAB$^+$ M—Br$^-$; 380 [NBA matrix]

Microanalysis EXP.: C, 45.66%; H, 9.73%; N, 11.70%; P, 12.90%. THEO.: C, 47.01%; H, 9.79%; N, 12.18%; P, 13.40%.

EXAMPLE 12

Synthesis of [(Me$_2$N)$_3$—P=N=PPh$_3$]$^+$Br$^-$ 14 mmol of a solution of dibromine diluted beforehand in 10 ml of dichloromethane at −5° C. are added dropwise to a solution of 14 mmol of triphenylphosphine in 70 ml of anhydrous dichloromethane. The mixture is stirred for 1 hour at a temperature of 0 to −5° C. (in situ formation of Ph$_3$PBr$_2$).

After addition of 1.5 equivalents of triethylamine, 14 mmol of iminotris(dimethylamino)phosphorane [(CH$_3$)$_2$N]$_3$P=NH in 14 ml of THF are then added to the solution of dibromotriphenylphosphorane Ph$_3$PBr$_2$.

After stirring overnight at room temperature, the reaction mixture is concentrated to dryness under reduced pressure. The solid residue is taken up in ether and then filtered off. The recovered precipitate is dissolved in 150 ml of dichloromethane and washed twice with 20 ml of distilled water. The organic phase is dried over MgSO$_4$ and then evaporated to dryness. The white solid obtained is suspended in 50 ml of ether and stirred for 30 minutes. The pure product is obtained by simple filtration and dried in a desiccator overnight over P$_2$O$_5$.

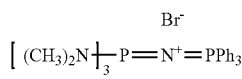

C$_{24}$H$_{33}$BrN$_4$P$_2$
519.4 g.mol$^{-1}$
White solid
67% yield $^{31}$P NMR (ppm) (CH$_2$Cl$_2$): 26.48 (d, J$^2{}_{P-P}$=37.3 Hz); 13.45 (d, J$^2{}_{P-P}$=37.3 Hz)

$^1$H NMR (ppm) (CDCl$_3$): 2.52 (d, CH$_3$, 18H, J$^3{}_{P-H}$=10.35 Hz); 7.57 to 7.44 (m, aromatic, 15H) ppm (CDCl$_3$): 152.72 (d, J$^4{}_{PC}$=3.01 Hz); 150.92 (d, J$^3{}_{PC}$=

$^{13}$C NMR 11.06 Hz) 148.68 (d, J$^2{}_{PC}$=13.20 Hz); 147.21 (dd, J$^1{}_{PC}$=108.64 Hz, J$^3{}_{PC}$=2.54 Hz); 56.25 (d, J$^2{}_{PC}$=4.52 Hz, MeN)

Mass: FAB$^+$ M—Br$^-$; 439 [NBA matrix]

Microanalysis EXP.: C, 45.66%; H, 9.73%; N, 11.70%; P, 12.90%. THEO.: C, 47.01%; H, 9.79%; N, 12.18%; P, 13.40%.

EXAMPLE 13

Synthesis of Bu$_3$—P=N=PBu$_3$$^+$Br$^-$

This example shows the advantage of the synthetic technique, although the product is not among the preferred products.

Thus, 14 mmol of a solution of dibromine diluted beforehand in 10 ml of dichloromethane at −5° C. are added dropwise to a solution of 14 mmol of tributylphosphine in 70 ml of anhydrous dichloromethane. The mixture is stirred for 1 hour at a temperature of 0 to −5° C. (in situ formation of Bu$_3$PBr$_2$).

After addition of 1.5 equivalents of triethylamine, 14 mmol of Bu$_3$P=NH (prepared by the action of 1 equivalent of BuLi on [Bu$_3$PNH$_2$]$^+$Br$^-$) in 14 ml of THF are then added to the solution of dibromotributylphosphorane Bu$_3$PBr$_2$.

After reacting overnight, the reaction mixture is concentrated to dryness and the residue recovered is taken up in 40 ml of THF. The solution is filtered and the organic phase containing the expected salt is evaporated to dryness. This salt is not entirely pure, since the residue contains about 25% of the starting aminophosphonium salt that we did not manage to separate out by recrystallization (on the basis of the phosphorus NMR). The precipitate is then heated at 160° C. for 5 hours until the residual starting salt has disappeared. Recrystallization of the residue from CCl$_4$ thus allows the expected product to be obtained in a yield of 52%.

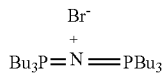

C$_{24}$H$_{54}$BrNP$_2$
498.549 g.mol$^{-1}$
YELLOW OIL
52% yield $^{31}$P{H} NMR (CH$_2$Cl$_2$): 36.3 ppm (Bu$_3$PNPBu$_3$, Br) (57.2 ppm (Bu$_3$PNH$_2$, Br))

$^1$H NMR (CDCl$_3$): 0.93 ppm (t, 18H, CH$_3$): 1.45 ppm (m, 24H, CH$_2$—CH$_2$); 2.03 ppm (m, 12H, —CH$_2$—P) (CDCl$_3$): 13.66 ppm (s, CH$_3$): 23.88 ppm (d, $^2$J$_{P-C}$=15.6

$^{13}$C NMR Hz, CH$_2$); 24.02 ppm (d, $^3$J$_{P-C}$=4.5 Hz, CH$_2$); 27.15 ppm (d/d, $^1$J$_{P-C}$=65.5 Hz, $^3$J$_{P-C}$≈0.4 Hz, CH$_2$)

Mass: FAB$^+$ M—Br$^-$; 418 [NBA matrix]

Microanalysis Awaiting

The invention claimed is:

1. A nucleophilic substitution process, comprising the steps of:

a) reacting a nucleophilic agent with an aromatic substrate substituted with a leaving group with creation of a bond between said nucleophilic agent and said substrate, on the carbon bearing the leaving group, and then, loss of said leaving group, in a polar aprotic solvent and in the presence of
a compound of formula (I)

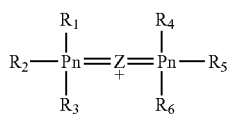

wherein:
R$_1$, R$_2$, R$_3$, R$_4$, R$_5$ and R$_6$, which are identical or different, are hydrocarbon containing radicals;
the Pn, are phosphorus; and
Z is a nitrogen, and with a molar ratio between the catalyst and the nucleophilic agent being not less than 0.1‰, and b) recovering the product made in step a).

2. The process as claimed in claim 1, wherein the aromatic substrate is further substituted with another leaving group.

3. The process as claimed in claim 1, wherein said nucleophilic agent is a halide.

4. The process as claimed in claim 1, wherein said halide is a fluoride.

5. The process as claimed in claim 4, wherein said leaving group is a chlorine atom.

6. A process for synthesizing a compound of formula (I)

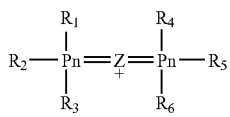

wherein:

$R_1$, $R_2$, $R_3$, $R_4$, $R_5$ and $R_6$, which are identical or different, are hydrocarbon containing radicals;

the Pn, are phosphorus; and

Z is a nitrogen, said process comprising the steps of:

a) successively or simultaneously reacting:
   a trivalent Pn compound;
   an iminoid of formula $(R_1)(R_2)(R_3)Pn=ZM$ wherein M represents a hydrogen or, optionally, a cation giving a well-dissociated salt; and, optionally, a reagent capable of giving a positively charged halogen without releasing water; and b) recovering the product obtained in step a).

7. The process as claimed in claim 6, wherein said reagent is a molecular halogen.

8. The process as claimed in claim 6, wherein said iminoid is subjected to the action of a halogen ($X_2$) before or during step a) to give one of the following reaction sequences:

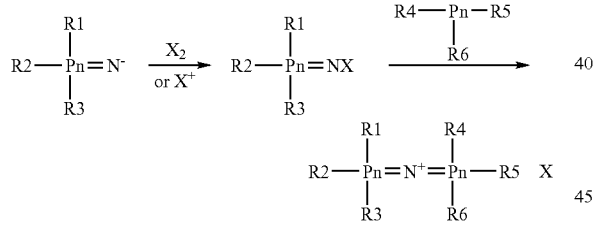

-continued

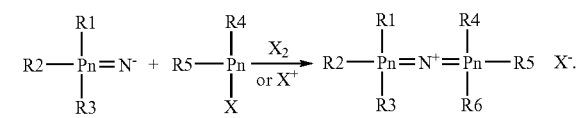

9. The process as claimed in claim 6, wherein said trivalent Pn compound is a phosphine of formula $P(R_4)(R_5)(R_6)$ and is subjected to the action of a halogen, to form, at least transiently, a halophosphonium halide of formula:

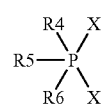

before or during step a).

10. The process as claimed in claim 6, wherein said trivalent Pn compound is halogenated and wherein no reagent capable of giving a positively charged halogen without releasing water is added, so as to perform one of the following non necessarily stoichiometric reactions:

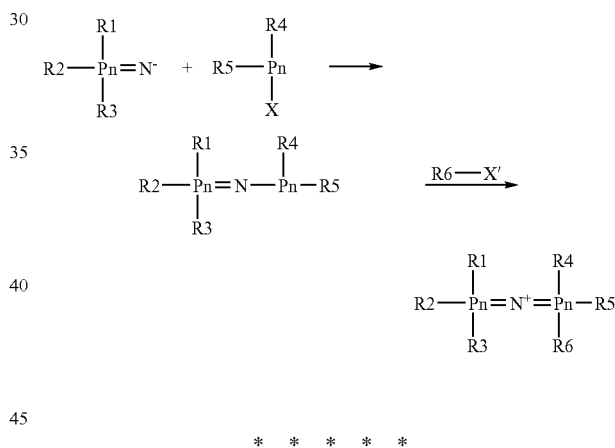

* * * * *